US005362743A

United States Patent [19]

Sarges et al.

[11] Patent Number: 5,362,743

[45] Date of Patent: Nov. 8, 1994

[54] AMINOQUINOLINE DERIVATIVES

[75] Inventors: Reinhard Sarges, Mystic, Conn.; Li-An Yeh, Cambridge, Mass.

[73] Assignee: Pfizer Inc., New York, N.Y.

[21] Appl. No.: 28,447

[22] Filed: Mar. 9, 1993

[51] Int. Cl.[5] .............................................. A61K 31/47

[52] U.S. Cl. .................................... 514/313; 546/159; 546/160

[58] Field of Search ................. 546/159, 160; 514/313

[56] References Cited

U.S. PATENT DOCUMENTS

| | | | |
|---|---|---|---|
| 4,343,804 | 8/1982 | Munson, Jr. et al. | 424/258 |
| 4,806,549 | 2/1989 | Ife et al. | 514/313 |
| 4,806,550 | 2/1992 | Ife et al. | 514/313 |
| 5,082,841 | 1/1992 | Brown et al. | 514/235.2 |
| 5,089,498 | 2/1992 | Ife et al. | 514/235.2 |
| 5,089,504 | 2/1992 | Ife et al. | 514/313 |
| 5,143,920 | 9/1992 | Ife et al. | 514/313 |

*Primary Examiner*—José G. Dees
*Assistant Examiner*—Samuel Barts
*Attorney, Agent, or Firm*—Peter C. Richardson; Paul H. Ginsburg

[57] ABSTRACT

Certain novel 3-acyl-4-amino-8-alkoxyquinoline compounds have been prepared, including their pharmaceutically-acceptable salts. These compounds are useful for inhibiting gastric acid secretion in mammals and therefore, are of value in therapy as anti-ulcer agents. They are also useful for treating osteoporosis in a mammalian subject afflicted with said condition. Methods for preparing these compounds from known starting materials are provided.

25 Claims, No Drawings

AMINOQUINOLINE DERIVATIVES

BACKGROUND OF THE INVENTION

This invention relates to new and useful 4-aminoquinoline derivatives of interest to those in the field of medicinal chemistry. More particularly, it is concerned with certain novel 3-acyl-4-amino-8-alkoxyquinoline compounds, including their pharmaceutically-acceptable salts. These particular compounds are useful as anti-ulcer agents, in view of their ability to inhibit gastric acid secretion in mammals. They are also useful for treating osteoporosis in a mammalian subject afflicted with said condition.

In the past, many attempts have been made by numerous investigators in the field of medicinal chemistry to obtain new and better anti-ulcer agents. For the most part, these efforts have often involved the synthesis and testing of many previously-unknown organic compounds, particularly in the area of organic heterocyclic bases, in an endeavor to determine their ability to inhibit the secretion of gastric juices in the stomach of a mammalian subject without causing the production of any substantial number of undesirable pharmacological side-effects. For instance, H. R. Munson, Jr. et al., in U.S. Pat. No. 4,343,804 refer to certain 4-amino-3-quinolinecarboxylic acids and esters to be useful for reducing gastric acidity and treating peptic ulcers in mammals, while R. J. Ife et al., in U.S. Pat. No. 4,806,549 refer to certain related 4-amino-3-(alkylcarbonyl)quinoline compounds as also being useful as gastric acid inhibitors. However, there is no known disclosure in the art of any 3-acyl-4-amino-8-alkoxyquinoline compounds having both antisecretory or anti-ulcer activity, together with a significant degree of anti-osteoporosis effects, prior to this particular invention.

SUMMARY OF THE INVENTION

In accordance with the present invention, it has now been rather surprisingly found that certain novel 3-acyl-4-amino-8-alkoxyquinoline compounds wherein the acyl moiety is a β-substituted propionyl group or a dihydro derivative of said group, are useful for inhibiting gastric acid secretion in mammals and therefore, are of value when employed as anti-ulcer agents. In addition, these particular compounds are also useful for treating osteoporosis in a mammalian subject afflicted with said condition. More specifically, the novel compounds of this invention are selected from the class consisting of 4-aminoquinoline derivatives of the formula:

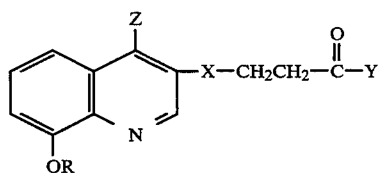

I or a pharmaceutically acceptable salt thereof, wherein R is methyl or ethyl; X is carbonyl or hydroxymethylene; Y is hydroxy, $C_1$–$C_6$ alkoxy, $C_1$–$C_8$ alkylamino or di($C_1$–$C_3$ alkyl)amino; and Z is di($C_1$–$C_8$ alkyl)amino, benzylamino, phenylethylamino or phenylamino, with each phenyl moiety being optionally ring-substituted with an alkyl group having from one to three carbon atoms. These novel compounds all possess anti-ulcer activity, particularly in view of their ability to inhibit the secretion of gastric acid in the body and therefore, are useful in the treatment of peptic ulcers and other like conditions. They are also additionally useful as potent anti-osteoporotic agents that can be effectively used for treating osteoporotic conditions in a mammalian subject. Furthermore, those carboxylic acid ester compounds of the aforegoing structural formula I wherein Y is $C_1$–$C_8$ alkoxy are all additionally useful as intermediates that lead to the corresponding carboxylic acids per se, wherein Y is hydroxy, and these latter compounds, in turn, are further still additionally useful as intermediates that lead to the corresponding carboxamide compounds wherein Y is other than hydroxy or $C_1$–$C_8$ alkoxy, as previously defined.

A preferred group of compounds of the present invention of particular interest in the present connection is that of structural formula I wherein R is methyl or ethyl, X is carbonyl or hydroxymethylene, Y is $C_1$–$C_6$ alkoxy, $C_1$–$C_8$ alkylamino or di($C_1$–$C_3$ alkyl)amino and Z is ring-substituted phenylamino. Particularly preferred compounds within this category include those wherein R is methyl, X is carbonyl, Y is ethoxy, $C_1$–$C_6$ alkylamino or di($C_1$–$C_3$ alkylamino) and Z is 2-methylphenylamino. Another preferred group of compounds of the present invention of equal importance is that of formula (I) wherein R is methyl, X is carbonyl, Y is $C_1$–$C_6$ alkoxy and Z is di($C_1$–$C_3$ alkyl)amino or optionally ring-substituted benzylamino. Particularly preferred compounds within this group include those wherein R is methyl, X is carbonyl, Y is ethoxy and Z is di($C_1$–$C_3$ alkyl)amino, benzylamino or 2-methylbenzylamino.

Of especially interest in this connection are such typical and preferred member compounds of the invention as 3-(3-ethoxycarbonylpropionyl)-8-methoxy-4-(2-methylphenylamino)quinoline, 4-benzylamino-3-(3-ethoxycarbonylpropionyl)-8-methoxyquinoline, 3-(3-ethoxycarbonylpropionyl)-8-methoxy-4-(2-methylbenzylamino)quinoline, 4-dimethylamino-3-(3-ethoxycarbonylpropionyl)-8-methoxyquinoline, 3-(3-ethoxycarbonyl-1-hydroxypropyl)-8-methoxy-4-(2-methylphenyl-amino)quinoline, 3-(3-carboxypropionyl)-8-methoxy-4-(2-methylphenylamino)quinoline, 3-(3-ethylaminocarbonylpropionyl)-8-methoxy-4-(2-methylphenylamino)quinoline, 3-(3-diethylaminocarbonylpropionyl)-8-methoxy-4-(2-methylphenylamino)quinoline and 3-(3-n-hexylaminocarbonylpropionyl)-8-methoxy-4-(2-methylphenylamino)quinoline, respectively.

Also included within the purview of this invention are various novel pharmaceutical compositions suitable for oral and parenteral administration and useful for treating a condition selected from gastric ulcers and osteoporosis in a mammalian subject in need of such treatment, said compositions comprising an amount of a 4-aminoquinoline compound of the formula I, or a pharmaceutically acceptable salt thereof, wherein R, X, Y and Z are each as hereinbefore defined, that is effective in treating such a condition in conjunction with a pharmaceutically acceptable carrier therefor.

DETAILED DESCRIPTION OF THE INVENTION

The process employed for preparing the novel compounds of structural formula I, wherein X is restricted to carbonyl and Y is exclusively $C_1$–$C_6$ alkoxy, are prepared by condensing a corresponding 3-acyl-8-alkoxy-4-haloquinoline compound of the formula:

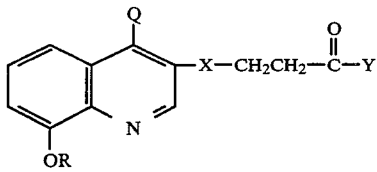

wherein R, X and Y are each as previously defined, and Q is an amine-displaceable "leaving" group, such as a halogen like chlorine or bromine, with at least an equivalent amount in moles of an appropriate amine base having the formula ZH wherein Z is also as previously defined for formula I. This particular condensation reaction is normally carried out in a reaction-inert polar aprotic organic solvent, such as anisole or a cyclic ether like dioxane or tetrahydrofuran, under substantially anhydrous conditions and at a temperature that ranges from about 15° C. up to about 100° C. for a period of at least about two hours (and usually, no more than about 72 hours), in order to ensure proper completeness of reaction. Preferred reaction conditions call for the use of an appropriately-substituted 4-chloroquinoline compound of structural formula II as starting material for the reaction and the use of tetrahydrofuran as the most suitably preferred organic solvent of choice, with the preferred reaction temperature generally ranging from about 45° C. up to about 65° C., until the desired condensation reaction is substantially complete. Upon completion of this step, the desired 3-acyl-4-amino-8-alkoxyquinoline ester of formula I, wherein X is carbonyl and Y is $C_1$–$C_6$ alkoxy, is most readily recovered from the reaction mixture, generally as the corresponding hydrohalide salt, by conventional means, e.g., by the use of suction filtration and the like, followed by recrystallization from a suitable solvent system, if necessary. Alternatively, the free base compounds may be first recovered from the reaction mixture by means of evaporation under reduced pressure, followed by column chromatography of the resulting residue over silica gel with the concomitant use of a suitable solvent system as eluant, etc.

As regards compounds of the invention of structural formula I wherein X is carbonyl and Y is exclusively hydroxy, these can readily be prepared from the corresponding ester final products wherein Y is $C_1$–$C_6$ alkoxy by simply hydrolyzing same in accordance with the conventional methods of organic chemistry. This is most readily accomplished in the present instance by simply treating the ester (Y=$C_1$–$C_6$ alkoxy) final products (now used as starting materials in the present instance) with an aqueous base, such as an alkali metal hydroxide like sodium hydroxide, in a suitable reaction-inert polar organic solvent, such as a lower alkanol ($C_1$–$C_3$) like ethanol or a cyclic ether like tetrahydrofuran, preferably at ambient temperatures (e.g., about 20° C.), to eventually generate the desired carboxylic acid (Y=OH) as a readily-recoverable precipitate upon acidification of the resulting reaction mixture.

Compounds of formula I wherein X is carbonyl and Y is exclusively $C_1$–$C_8$ alkylamino or di($C_1$–$C_3$ alkyl)amino can be prepared from the corresponding carboxylic acid intermediate products wherein Y is hydroxy by first converting same into a mixed anhydride, in accordance with standard organic procedures, followed by treatment of the latter type compound with either a $C_1$–$C_8$ alkylamine or a di($C_1$–$C_3$ alkylamine) to finally form the desired amide final product of formula I wherein Y is either $C_1$–$C_8$ alkylamino or di($C_1$–$C_3$ alkyl)amino. More particularly, the amidation step is readily accomplished by first treating the starting acid (Y=OH) with a suitable activating agent, such as a branched-chain lower alkyl ($C_3$–$C_5$) haloformate like isobutyl chloroformate, in the presence of a base, such as a tertiary-amine like triethylamine or N-methylmorpholine, at temperatures ranging from about 0° C. to as low as about −15° C., to yield the mixed anhydride intermediate, which is then reacted with the appropriate primary or secondary alkylamine base compound at temperatures ranging from about −10° C. up to about 25° C. to eventually yield the corresponding amide final product where Y is other than hydroxy or $C_1$–$C_6$ alkoxy.

Lastly, compounds of the invention of formula I wherein X is restricted to hydroxymethylene can be prepared from the corresponding keto-ester final products wherein X is carbonyl and Y is $C_1$–$C_6$ alkoxy by simply reducing same in accordance with standard organic procedure. This particular reduction step is most readily accomplished by subjecting the keto-ester starting material to the selective action of a carbonyl reducing agent in a polar protic or an aprotic solvent at temperatures ranging from about 0° C. up to about 25° C., until the reduction reaction to form the desired alcohol ester compound is substantially complete. Preferred carbonyl reducing agents for these purposes include the alkali metal borohydrides (e.g., sodium borohydride) and the like, while preferred polar protic solvents for use in this connection include water and the lower alkanols ($C_1$–$C_4$) such as methanol, ethanol and isopropanol etc. Upon completion of the aforesaid reduction reaction, the desired alcohol-ester final product (wherein X is hydroxymethylene and Y is $C_1$–$C_6$ alkoxy) is readily recovered from the spent reaction mixture in accordance with various standard techniques well-known to those skilled in the art.

The formula II 4-haloquinoline compounds required for preparing the novel formula I 4-aminoquinoline final products of the present invention are prepared by halogenating, i.e., chlorinating or brominating, the corresponding 3-acyl-8-alkoxy-4-hydroxyquinoline ester compounds with phosphorous oxychloride or phosphorus oxybromide, as the case may be, in accordance with the general procedure described by W. O. Kermack et al. in the *Journal of the Chemical Society* (London), p. 1389 (1951). This particular halogenation reaction essentially involves heating the 4-hydroxyquinoline starting material with the phosphorus oxychloride or bromide halogenating agent at elevated temperatures, with the preferred temperature usually being found at or near the reflux temperature of the resulting mixture. Upon completion of the reaction, the desired 4-haloquinoline intermediate product is then easily isolated from the reaction mixture in accordance with standard techniques (see Preparation C for further details).

The 4-hydroxyquinoline compounds used as starting materials in the above described halogenation reaction, viz., the corresponding 3-acyl-8-alkoxy-4-hydroxyquinoline ester compounds, are prepared by condensing an appropriately-substituted aniline compound, such as o-anisidine, with an appropriate β-ketoadipic acid di-ester, such as diethyl β-ketoadipate, in the presence of an ortho ester such as triethyl orthoformate, at an elevated temperature (e.g., at about 140° C.), so as to form an intermediate condensation product, viz., o-[2-ethoxycarbonyl-2-(3-ethoxycarbonylpropionyl)-1-ethylideneamino]anisole, which is then immediately thereafter cyclized in a high boiling solvent, such as diphenyl ether, essentially in accordance with the general procedure described by C. C. Price et al., in the *Journal of the American Chemical Society*, Vol. 68, p. 1204 (1946). In this way, there is readily provided a facile method for generating a 4-hydroxyquinoline compound that is substituted in the 3-position with a ketoalkyl ester group, e.g., the desired 3-(3-ethoxycarbonylpropionyl) group, for the present purpose at hand (see Preparations A-B for further details).

Inasmuch as the formula I compounds wherein Y is other than hydroxy are basic compounds, they necessarily can and do form salts with various inorganic and organic acids. Although such salts must be pharmaceutically acceptable for administration to animals, including humans, it is often desirable in practice to initially isolate the 4-aminoquinoline base compound from the reaction mixture as a pharmaceutically unacceptable salt and then simply convert the latter substance back to the free base compound by treatment with an alkaline reagent and thereafter convert the latter free base compound to a pharmaceutically acceptable acid addition salt. The acid addition salts of the 4-aminoquinoline base compounds of this invention are readily prepared by treating the base compound with a substantially equivalent amount of the chosen mineral or organic acid in an aqueous solvent medium or in a suitable organic solvent, such as a lower alkanol ($C_1$–$C_3$) like methanol or ethanol. Upon careful evaporation of the solvent, the desired solid salt is readily obtained.

The acids which are used to prepare the pharmaceutically acceptable acid addition salts of the aforementioned 4-aminoquinoline base compounds of this invention are those which form non-toxic acid addition salts, i.e., salts containing pharmacologically-acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis(2-hydroxy-3-naphthoate)] salts.

As previously indicated, the 3-acyl-4-amino-8-alkoxyquinoline compounds of present invention useful as inhibitors of gastric acid secretion for the control of peptic ulcers (i.e., they are anti-ulcer agents) in mammals, including humans. In addition, they also have the surprising ability to inhibit bone resorption by osteoclasts in a bone slice assay and hence, are also able to function as anti-osteoporotic agents in mammals, including humans. More particularly, these compounds have been found to exert their anti-secretory effect by a reversible inhibition of the gastrointestinal enzyme known as $H^+/K^+$-ATPase (E. Fellenius et al., in *Nature*, Vol. 290, p. 159 (1981), while their antiosteoporotic activity is demonstrated by their ability to reverse or inhibit bone resorption by osteoclasts in a bone slice assay, as aforesaid, when tested for this particular activity according to the method described by T. J. Chambers et al., in *Endocrinology*, Vol. 116, p. 234 (1985). Furthermore, the herein described compounds of the present invention produce their beneficial results without causing any significant untoward pharmacological side effects.

The novel 3-acyl-4-amino-8-alkoxyquinoline compounds of this invention can be administered via either the oral or parenteral routes. In general, these compounds are most desirably administered in doses ranging from about 10 mg up to about 1000 mg per day, although variations will necessarily occur depending upon the weight and condition of the subject being treated and the particular route of pharmaceutical administration chosen. However, a dosage level that is in the range of from about 0.15 mg to about 15.0 mg per kg. of body weight per day is most desirably employed. Nevertheless, variations may still occur depending upon the species of animal being treated and its individual response to the compound being adminstered, as well as on the type of pharmaceutical formulation chosen and the time period and interval at which such administration is carried out. In some instances, dosage levels below the lower limit of the aforesaid range may be more than adequate, while in other cases still larger doses may be employed without causing harmful side effects provided that such higher dose levels are first divided into small doses for administration throughout the day.

The 3-acyl-4-amino-8-alkoxyquinoline compounds of this invention may be administered alone or in combination with pharmaceutically acceptable carriers by either of the two routes previously indicated, and such administration can be carried out in single or multiple dosages. More particularly, the novel therapeutic agents of the invention can be administered in a wide variety of different dosage forms, e.g., they may be combined with various pharmaceutically acceptable inert carriers or diluents in the form of tablets, capsules, lozenges, troches, hard candies, powders, sprays, suppositories, jellies, aqueous suspensions, injectable solutions, elixirs and syrups. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration, the active ingredient therein may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these 3-acyl-4-amino-8-alkoxyquinoline compounds in either sesame or peanut oil or in aqueous propylene glycol may be employed. The aqueous solutions should be suitably buffered (preferably, pH greater than 8), if necessary, and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical practice and techniques well-known to those skilled in the art.

The activity of the compounds of the present invention as anti-ulcer agents, useful in the treatment of gastric disease in mammals, such as peptic ulcers, etc., is assessed by their ability to inhibit gastric $H^+/K^+$-ATPase, using isolated porcine gastric microsomes and essentially employing a modification of the method first described by G. Saccomani et al., as initially reported in *Biochimica Biophysica Acta*, Vol. 465, p. 311 (1977). The modification involves preparing the microsomes from hog gastric mucosa according to the procedure first described by L-A. Yeh et al., in *Membrane Biochemistry*, Vol. 9, p. 129 (1991). The $H^+/K^+$-ATPase enzyme activity is assayed according to the procedure described by N. Chang et al., in *Biochimica Biophysica Acta*, Vol. 464, p. 313 (1977), using a medium containing 10 ¾g protein, 3 mM ATP, 50 mM Tris-HCl (pH 7.4) and 2 mM $MgCl_2$ with or without 10 mM KCl in a final volume of 1.1 mL. The incubation step is initially carried out at 37° C. for a period of 15 minutes. The reaction is then terminated by the addition of 100 μL of 50% TCA (trichloroacetic acid). Phosphate release is next measured spectrophotometrically in the manner described by C. H. Fiske et al., in the *Journal of Biological Chemistry*, Vol. 66, p. 375 (1925). Under these particular test conditions, 3-(3-ethoxycarbonylpropionyl)-8-methoxy-4-(2-methylphenylamino)quinoline, a typical and preferred agent of the present invention, was found to effectively inhibit the gastric $H^+/K^+$-ATPase enzyme both reversibly and specifically within an $IC_{50}$ value range of 10–20 μM (with close to 50% inhibition being observed at 10 μM).

The activity of the compounds of the present invention as anti-osteoporotic agents, useful for the treatment of osteoporosis in a mammalian subject afflicted with said condition, is readily assessed by their ability to effectively inhibit bone resorption by osteoclasts in a bone slice assay, as determined by the method described by T. J. Chambers et al, in the *Journal of Cell Science*, Vol. 76, p. 155, (1985), as well as in *Endocrinology*, Vol. 116, p. 234 (1985). In this assay, osteoclasts are mechanically disaggregated from neonatal rat long bones into Hepes-buffered medium 199 (available from Flow Laboratories of Irvine, England in the United Kingdom). The suspension is agitated with a pipette and the larger fragments were allowed to settle for a period of 30 seconds. The cells are then added to two wells of a multiwell-dish containing bone slices, with each of said slices measuring 2.5 $mm^2$. After incubating at 37° C. for a period of 15 minutes, the aforesaid bone slices are then removed, washed in medium 199 and placed in individual wells of a 96-well plate (also available from Flow Laboratories). These latter bone slices are then incubated overnight in a total volume of 200 mL of culture medium consisting of 10% newborn calf-serum (from Flow Laboratories) in Hanks-buffered MEM (also from Flow Laboratories) in the presence or absence of the test compound. Bone resorption is quantified by means of scanning electron microscopy. Bone slices are immersed in 10% aqueous sodium hypochlorite (NaOCl) for a period of ten minutes to remove cells, and next washed in distilled water, dried and sputter-coated with gold. The entire surface of each bone slice is then examined in a Cambridge S90 scanning electron microscope (available from Cambridge Instruments of Cambridge, England in the United Kingdom). The number and size of the osteoclastic excavations, and the plan area of bone resorbed is recorded. Differences between groups are then analyzed by means of Student's t-Test. Under the conditions of this particular test procedure, 3-(3-ethoxycarbonylpropionyl)-8-methoxy-4-(2-methylphenylamino)quinoline was found to be a potent inhibitor of lacunae formation and of resultant bone resorption by isolated osteoclasts in a bone slice assay carried out in a dose-responsive manner, with statistically significant inhibition occurring at a concentration level as low as $10^{-7}$ M (0.1 μM).

PREPARATION A

A mixture consisting of 5.0 g (0.041 mole) of o-anisidine (available from the Aldrich Chemical Company, Inc. of Milwaukee, Wis.), 8.86 g (0.041 mole) of β-ketoadipic acid diethyl ester (available from Sigma Chemical Company of St. Louis, Mo.) and 6.07 g (0.041 mole) of triethyl orthoformate (also available from Aldrich) was placed in an open reaction flask and heated to 140° C. for a period of three hours, at which point no further amount of ethanol by-product formation could be observed to evolve from the reaction mixture. Upon completion of this step, the spent reaction mixture was allowed to cool to ambient temperatures (ca. 20° C.) on standing overnight for a period of approximately 16 hours. The resulting residual solid was thereafter triturated with petroleum ether and filtered to give 11.53 g (82%) of pure o-[2-ethoxycarbonyl-2-(3-ethoxycarbonylpropionyl)-1-ethylideneamino]anisole. The pure product was characterized by means of mass spectrum (MS) analysis and nuclear magnetic resonance (NMR) data.

MS and NMR Data: Mass Spectrum, m/e 349; $^1H$ NMR($CDCl_3$) consistent with product.

PREPARATION B

The total amount (11.53 g, 0.0336 mole) of the above o-anisidine derivative (the product of Preparation A) was then added in small portions to 100 mL of boiling diphenyl ether. Upon completion of this step, the resulting reaction mixture was refluxed for a period of four hours and then slowly allowed to cool down to room temperature (ca. 20° C.). Trituration of the residual product with petroleum ether, followed by suction filtration then gave 4.52 g (45%) of pure 3-(3-ethoxycarbonylpropionyl)-4-hydroxy-8-methoxyquinoline. The pure product was characterized by means of mass spectrum (MS) analysis and nuclear magnetic resonance (NMR) data.

MS and NMR Data: Mass spectrum, m/e 302; $^1H$ NMR ($CDCl_3$) consistent with product.

PREPARATION C

A well-stirred mixture consisting of 4.44 g (0.147 mole) of 3-(3-ethoxycarbonylpropionyl)-4-hydroxy-8-methoxyquinoline (the product of Preparation B) combined with 10 mL of phosphorus oxychloride was heated to reflux for a period of 1.5 hours. Upon completion of this step, the resulting reaction mixture was allowed to cool to ambient temperatures (ca. 20° C.) and then evaporated to near dryness while under reduced pressure. The residual product mass was next dissolved in methylene chloride, washed with water and subsequently dried over anhydrous sodium sulfate. After removal of the drying agent by means of suction filtration and the solvent by means of evaporation under reduced pressure, there was eventually obtained a crude residual oil that was thereafter chromatographed over silica gel using 1.0% methanol in chloroform as the eluent. Isolation of the major LP (less lipophilic) material then gave a clear orange oil, which subsequently crystallized on standing to ultimately afford 1.72 g (36%) of pure 4-chloro-3-(3-ethoxycarbonylpropionyl)-8-methoxyquinoline. The pure product was characterized by means of mass spectrum (MS) analysis and nuclear magnetic resonance (NMR) data.

MS and NMR Data: Mass spectrum, m/e 321; $^{1}H$ NMR($CDCl_3$) consistent with product.

EXAMPLE 1

In a flame-dried, three-necked round-bottomed reaction flask equipped with reflux condenser, magnetic stirring bar and addition funnel, there were placed 1.72 g (0.00535 mole) of 4-chloro-3-(3-ethoxycarbonylpropionyl)-8-methoxyquinoline (the product of Preparation C) dissolved in 15 mL of dry tetrahydrofuran. Stirring was commenced and the resulting organic solution was then treated dropwise with a solution consisting of 573 mg (0.00535 mole) of o-toluidine (available from the Aldrich Chemical Company, Inc. of Milwaukee, Wis.) dissolved in 15 mL of dry tetrahydrofuran. The resulting reaction mixture was then stirred and heated to 60° C. and thereafter kept at that temperature for a period of approximately 16 hours (i.e., overnight). Upon completion of this step, the final reaction mixture was slowly allowed to cool to ambient temperatures (ca. 20° C.) and the yellow precipitate which resulted was subsequently collected by means of suction filtration and air-dried on the filter funnel to constant weight. Recrystallization of the latter crude salt material from methylene chloride/ethyl acetate/petroleum ether then gave 1.75 g (76%) of pure 3-(3-ethoxycarbonylpropionyl)-8-methoxy-4-(2-methylphenylamino)quinoline as the hydrochloride salt, m.p. 210°–211° C. The pure product was further characterized by means of mass spectrum (MS) analysis and nuclear magnetic resonance (NMR) data, in addition to elemental analysis.

MS and NMR Data: Mass spectrum, m/e 392; $^{1}H$ NMR (DMSO-$d_6$) consistent with product.

Anal. Calcd. for $C_{23}H_{24}N_2O_4.HCl$: C, 64.41; H, 5.87; N, 6.53. Found: C, 64.25, H, 5.80; N, 6.29.

EXAMPLE 2

In a flame-dried, three-necked round-bottomed reaction flask equipped with reflux condenser, magnetic stirring bar and rubber septum, there were placed 3.0 g (0.0093 mole) of 4-chloro-3-(3-ethoxycarbonylpropionyl)-8-methoxyquinoline (the product of Preparation C) dissolved in 30 mL of dry tetrahydrofuran. Stirring was commenced and to the resulting ethereal solution were then added with 2.0 g (0.0186 mole) of benzylamine (available from the Eastman Kodak Company of Rochester, N.Y.), which was added over a five-minute period at room temperature (ca. 20° C.). The well-stirred reaction mixture was then heated to 60° C. and thereafter kept at that temperature for a period of six hours. Upon completion of this step (as revealed by thin layer chromatography (TLC) analysis), the final reaction mixture was filtered to remove precipitated benzylamine hydrochloride and the filtrate was subsequently evaporated to near dryness while under reduced pressure to afford a solid material as the residue. Trituration of the latter material with diethyl ether then gave 880 mg (22%) of essentially pure 4-benzylamino-3-(3-ethoxycarbonylpropionyl)-8-methoxyquinoline as the free base compound: mass spectrum, m/e 392; NMR ($CDCL_3$) consistent with product. The latter batch of material was next dissolved in dry benzene and thereafter treated with anhydrous hydrogen chloride gas to ultimately yield 320 mg (8%) of pure 4-benzylamino-3-(3-ethoxycarbonylpropionyl)-8-methoxyquinoline as the hydrochloride salt (in the form of a monohydrate), m.p. 201°–202° C. after one recrystallization from methanol-diethyl ether. The pure product was further characterized by means of mass spectrum (MS) analysis, in addition to elemental analysis. Mass spectrum, m/e 392.

Anal. Calcd. for $C_{23}H_{24}N_2O_4.HCL.H_2O$: C, 61.81; H, 6.09; N, 6.27. Found: C, 61.93; H, 6.00; N, 6.12.

EXAMPLE 3

In a flame-dried, three-necked round-bottomed reaction flask equipped with reflux condenser, magnetic stirring bar and rubber septum, there was placed 1.0 g (0.0031 mole) of 4-chloro-3-(3-ethoxycarbonylpropionyl)-8-methoxyquinoline (the product of Preparation C) dissolved in 10 mL of dry tetrahydrofuran. Stirring was commenced and 0.8 mL (750 mg, 0.0062 mole) of 2-methylbenzylamine (available from the Aldrich Chemical Company, Inc. of Milwaukee, Wis.), was added over a two-minute period at room temperature (ca. 20° C.). The well-stirred reaction mixture was then heated to 60° C. and thereafter kept at that temperature for a period of approximately 16 hours (i.e., overnight). Upon completion of this step, the resulting reaction mixture was then filtered to remove 2-methylbenzylamine hydrochloride that had precipitated from the mixture and the filtrate was subsequently evaporated to near dryness while under reduced pressure to afford a crude solid product as the residue. The latter material was then purified by means of column chromatography over silica gel, using a 1% solution of diethylamine in ethyl acetate as the eluant. In this manner, there was ultimately obtained a 43 mg (3%) yield of pure 3-(3-ethoxycarbonylpropionyl)-8-methoxy-4-(2-methylbenzylamino)quinoline as the free base compound (isolated as a 0.25 hydrate), m.p. 152°–155° C. The pure product was further characterized by means of mass spectrum (MS) analysis and nuclear magnetic resonance (NMR) data, in addition to elemental analysis.

MS and NMR Data: Mass spectrum, m/e and $^{1}H$ NMR ($CDCl_3$) both consistent with product.

Anal. Calcd. for $C_{24}H_{26}N_2O_4.0.25H_2O$; C, 70.14; H, 70.14; H, 6.50; N, 6.82. Found: C, 69.72; H, 6.48; N, 6.62.

EXAMPLE 4

In a flame-dried, three-necked round-bottom reactions flask equipped with reflux, condenser, magnetic stirring bar and gas-inlet tube, there was placed 1.0 g (0.0031 mole) of 4-chloro-3-(3-ethoxycarbonylpropionyl)-8-methoxyquinoline (the product of Preparation C) dissolved in 15 mL of dry tetrahydrofuran. Stirring was commenced and gaseous dimethylamine was then bubbled into the stirred ethereal solution at room temperature (ca. 20° C.) for a period of five minutes. The resulting reaction mixture was then stirred at room temperature under a nitrogen blanket for a period of three days. Upon completion of this step, the final reaction mixture was next concentrated in vacuo to an orange oil which was subsequently dissolved in chloroform to give a clear solution. The clear chloroform solution thus obtained was then successively washed with three-separate fresh portions of water, aqueous sodium bicarbonate and brine, followed by drying over anhydrous magnesium sulfate. After removal of the drying agent by means of suction filtration and the solvent by means of evaporation under reduced pressure, there was eventually obtained a residual oil. The latter material was next dissolved in diethyl ether and treated with anhydrous hydrogen chloride gas to ultimately yield 137 mg (14%) of pure 4-dimethylamino-3-(3-ethoxycarbonylpropionyl)-8-methoxyquinoline as the hydrochloride salt (in the form of a monohydrate), m.p. 134°-135° C. (decomp.). The pure product was further characterized by means of mass spectrum (MS) analysis and nuclear magnetic resonance (NMR) data, in addition to elemental analysis.

MS and NMR Data: Mass spectrum, m/e 330; $^1$H NMR ($CDCl_3$) consistent with product.

Anal. Calcd. for $C_{18}H_{22}N_2O_4$.HCL.$H_2O$: C, 56.18; H, 6.55; N, 7.28. Found: C, 55.75; H, 6.59; N, 6.90.

EXAMPLE 5

A well-stirred suspension consisting of 3.59 g (0.00915 mole) of 3-(3-ethoxycarbonylpropionyl)-8-methoxy-4-(2-methylphenylamino)-quinoline (the product of Example 1) in 200 mL of methanol was cooled to 5° C. and 173 mg. (0.0045 mole) of sodium borohydride (available from the Aldrich Chemical Company, Inc. of Milwaukee, Wis.) was immediately thereafter slowly added in small-divided portions, followed by continued stirring of the reaction mixture at 5° C. for a period of 45 minutes. At this point, a fresh batch of 90 mg of sodium borohydride was added to the stirred reaction mixture and further stirring was then continued at 5° C. for a period of one hour. Upon completion of this step, the pH of the resulting homogeneous solution was next adjusted to a value of pH 7 by the careful addition of glacial acetic acid, followed by filtration and subsequent evaporation of the resulting filtrate under reduced pressure to eventually give a crystalline product as the residue. Recrystallization of the latter material from methanol-water then gave a nearly quantitative yield of pure 3-(3-ethoxycarbonyl-1-hydroxypropyl)-8-methoxy-4-(2-methyl-phenylamino)quinoline as a partial hemihydrate, m.p. 133°-135° C. The pure product was further characterized by means of mass spectrum (MS) analysis and nuclear magnetic resonance (NMR) data, in addition to elemental analysis.

MS and NMR Data: Mass spectrum, m/e 394; NMR (DMSO-$d_6$) consistent with product.

Anal. Calcd. for $C_{23}H_{26}N_2O_4$.0.75 $H_2O$: C, 67.71; H, 6.79; N, 6.87. Found: C, 68.02; H, 6.42; N, 6.80.

EXAMPLE 6

A 1.2 g (0.0028 mole) batch of 3-(3-ethoxycarbonylpropionyl)-8-methoxy-4-(2-methylphenylamino)quinoline (the product of Example 1) was suspended in 30 mL of ethanol with constant agitation and subsequently treated with 3.0 ml. of 0.5N aqueous sodium hydroxide, followed by stirring overnight at room temperature (ca. 20° C.) for a period of approximately 16 hours. At this point, a thick yellow precipitate had formed and the reaction mixture was next concentrated in vacuo to remove the ethanol and the pH was adjusted to pH 5.0 with added aqueous hydrochloric acid. Upon completion of this step, the resulting yellow solids were subsequently collected by means of suction filtration and thereafter washed on the filter funnel with water and petroleum ether to ultimately afford 1.02 g (100%) of pure 3-(3-carboxypropionyl)-8-methoxy-4-(2-methylphenylamino)quinoline, m.p. 263°-265° C. The pure product was further characterized by means of mass spectrum (MS) analysis and nuclear magnetic resonance (NMR) data, in addition to elemental analysis.

MS and NMR data: Mass spectrum, m/e 364; $^1$H NMR(DMSO-$d_6$) consistent with product.

Anal. Calcd. for $C_{21}H_{20}N_2O_4$: C 69.22; 4, 5.53; N, 6.69. Found: C, 69.38; H, 5.65; N, 7.30.

EXAMPLE 7

A 250-mg (0.00069 mole) portion of 3-(3-carboxypropionyl)-8-methoxy-4-(2-methylphenylamino)quinoline (the product of Example 6) was placed in a flame-dried three-necked, round-bottomed reaction flask equipped with a reflux condenser, magnetic stirring bar and rubber septum, and suspended in 5 mL of dry tetrahydrofuran with the aid of constant agitation. The resulting suspension was cooled to a temperature of −10° C. and 70 mg (0.00069 mole, 76 μL) of N-methylmorpholine (available from the Aldrich Chemical Company, Inc. of Milwaukee, Wis.) and 94 mg (0.00069 mole, 89 μL) of isobutyl chloroformate (also available from Aldrich) were then successively added to the well-stirred reaction mixture via a syringe. The resulting mixture was then allowed to stir at −10° C. for a period of 30 minutes, at which point 79 mg (0.00123 mole, 100 μL) of 70% aqueous ethylamine was added and the mixture was allowed to warm to room temperature (ca. 20° C.) with constant agitation for a period of two hours. Upon completion of this step, the final reaction mixture was next filtered and then evaporated to near dryness while under reduced pressure to yield a residual solid product. The latter substance was subsequently dissolved in ethyl acetate, and the resulting organic solution was washed with water and dried over anhydrous magnesium sulfate. After removal of the drying agent by means of suction filtration and the solvent by means of evaporation under reduced pressure, there was eventually obtained the desired N-ethyl amide final product. Recrystallization of the latter material from methanol-water then gave 75 mg (27%) of pure 3-(3-ethylaminocarbonylpropionyl)-8-methoxy-4-(2-methylphenylamino)-quinoline as the hemihydrate, m.p. 88.5°-90° C. The pure product was further characterized by means of mass spectrum (MS) analysis and nuclear magnetic resonance (NMR) data, in addition to elemental analysis.

MS and NMR data: Mass spectrum, m/e 391; $^1$H NMR ($CDCl_3$) consistent with product.

Anal. Calcd. for $C_{23}H_{25}N_3O_3$.0.5$H_2O$: C, 68.98; H, 6.54; N, 10.49. Found: C, 68.90; H, 6.33; N, 10.34.

EXAMPLE 8

The procedure described in Example 7 was repeated except that diethylamine was the reagent of choice employed in lieu of ethylamine, using the same molar proportions as before. In particular this case, the corresponding final product obtained was 3-(3-diethylaminocarbonylpropionyl)-8-methoxy-4-(2-methylphenylamino)quinoline (isolated as a hydrate), m.p.

151°–153° C. after one recrystallization from methanol-water. The pure product was further characterized by means of mass spectrum (MS) analysis and nuclear magnetic resonance (NMR) data, in addition to elemental analysis.

MS and NMR Data: Mass spectrum, m/e 419; $^1H$ NMR ($CDCl_3$) consistent with product.

Anal. Calcd. for $C_{25}H_{29}N_3O_3$.1.25 $H_2O$; C, 67.93; H, 7.18; N, 9.51. Found: C, 67.87; H, 6.89; N, 9.35.

EXAMPLE 9

The procedure described in Example 7 was repeated except that n-hexylamine was the reagent of choice employed in place of ethylamine, using the same molar proportions as before. In this particular case, the corresponding final product obtained was 3-(3-n-hexylaminocarbonylpropionyl)-8-methoxy-4-(2-methylphenylamino)quinoline (isolated as the hemihydrate), m.p. 59°–60° C. after one recrystallization from methanol-water. The pure product was further characterized by means of mass spectrum (MS) analysis and nuclear magnetic resonance (NMR) data, in addition to elemental analysis.

MS and NMR Data: Mass spectrum, m/e 447; NMR ($CDCl_3$) consistent with product.

Anal. Calcd. for $C_{27}H_{33}N_3O_3$.05$H_2O$: C, 71.03; H, 7.51; N, 9.20. Found: C, 71.53; H, 7.38; N, 9.17.

We claim:

1. A 4-aminoquinoline compound of the formula:

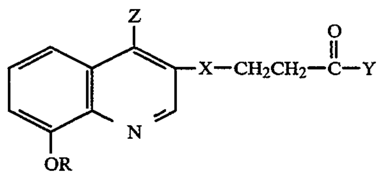

or a pharmaceutically acceptable salt thereof, wherein

R is methyl or ethyl;

X is carbonyl or hydroxymethylene;

Y is hydroxy, $C_1$–$C_6$ alkoxy, $C_1$–$C_8$ alkylamino or di($C_1$–$C_3$ alkyl)amino; and Z is di($C_1$–$C_3$ alkyl)amino, benzylamino, phenylethylamino or phenylamino, with each phenyl moiety being optionally ring-substituted with an alkyl group having from one to three carbon atoms.

2. A compound as claimed in claim 1 wherein R is methyl.

3. A compound as claimed in claim 2 wherein X is hydroxymethylene.

4. A compound as claimed in claim 2 wherein X is carbonyl.

5. A compound as claimed in claim 3 wherein Y is $C_1$–$C_6$ alkoxy and Z is ring-substituted phenylamino.

6. A compound as claimed in claim 4 wherein Y is $C_1$–$C_6$ alkoxy, $C_1$–$C_8$ alkylamino or di($C_1$–$C_3$ alkyl)amino.

7. A compound as claimed in claim 4 wherein Y is hydroxy and Z is ring-substituted phenylamino.

8. A compound as claimed in claim 6 wherein Y is $C_1$–$C_6$ alkoxy and Z is ring-substituted phenylamino.

9. A compound as claimed in claim 6 wherein Y is $C_1$–$C_6$ alkoxy and Z is optionally ring-substituted benzylamino.

10. A compound as claimed in claim 6 wherein Y is $C_1$–$C_6$ alkoxy and Z is di($C_1$–$C_3$)alkylamino.

11. A compound as claimed in claim 6 wherein Y is $C_1$–$C_8$ alkylamino and Z is ring-substituted phenylamino.

12. A compound as claimed in claim 6 wherein Y is di($C_1$–$C_3$)alkylamino and Z is ring-substituted phenylamino.

13. A compound as claimed in claim 5 wherein Y is ethoxy and Z is 2-methylphenylamino.

14. A compound as claimed in claim 7 wherein Y is hydroxy and Z is 2-methylphenylamino.

15. A compound as claimed in claim 8 wherein Y is ethoxy and Z is 2-methylphenylamino.

16. A compound as claimed in claim 9 wherein Y is ethoxy and Z is benzylamino.

17. A compound as claimed in claim 9 wherein Y is ethoxy and Z is 2-methylbenzylamino.

18. A compound as claimed in claim 10 wherein Y is ethoxy and Z is dimethylamino.

19. A compound as claimed in claim 11 wherein Y is ethylamino and Z is 2-methylphenylamino.

20. A compound as claimed in claim 11 wherein Y is n-hexylamino and Z is 2-methylphenylamino.

21. A compound as claimed in claim 12 wherein Y is diethylamino and Z is 2-methylphenylamino.

22. The free organic base of the 4-aminoquinoline compound as claimed in claim 15, which is 3-(3-ethoxycarbonyl)propionyl-8-methoxy-4-(2-methylphenylamino)quinoline.

23. A pharmaceutical composition suitable for oral or parenteral administration and useful for treating a condition selected from gastric ulcer and osteoporosis in a mammalian subject in need of such treatment, said composition comprising an amount of a 4-aminoquinoline compound as claimed in claim 1 that is effective in treating such a condition and a pharmaceutically acceptable carrier therefor.

24. A method for inhibiting gastric acid secretion in the treatment of gastric ulcers in a mammalian subject afflicted with said condition, which comprises administering to said subject a therapeutically-effective anti-ulcer amount of a 4-aminoquinoline compound as claimed in claim 1.

25. A method for treating osteoporosis in a mammalian subject afflicted with said condition, which comprises administering to said subject a therapeutically-effective anti-osteoporosis amount of a 4-aminoquinoline compound as claimed in claim 1.

* * * * *